United States Patent
Hernandez et al.

(10) Patent No.: US 9,758,536 B2
(45) Date of Patent: Sep. 12, 2017

(54) PHOSPHOLIPID COMPOSITIONS ENRICHED FOR PALMITOLEIC, MYRISTOLEIC OR LAUROLEIC ACID, THEIR PREPARATION AND THEIR USE IN TREATING METABOLIC AND CARDIOVASCULAR DISEASE

(71) Applicant: OMEGA PROTEIN CORPORATION, Houston, TX (US)

(72) Inventors: Ernesto Hernandez, Houston, TX (US); Marina Rusli, Katy, TX (US); Mark Griffin, Tomball, TX (US)

(73) Assignee: Omega Protein Corporation, Houston, TX (US)

( * ) Notice: Subject to any disclaimer, the term of this patent is extended or adjusted under 35 U.S.C. 154(b) by 1 day.

(21) Appl. No.: 14/362,572

(22) PCT Filed: Dec. 6, 2012

(86) PCT No.: PCT/US2012/068317
§ 371 (c)(1),
(2) Date: Jun. 3, 2014

(87) PCT Pub. No.: WO2013/086243
PCT Pub. Date: Jun. 13, 2013

(65) Prior Publication Data
US 2014/0364399 A1 Dec. 11, 2014

Related U.S. Application Data

(60) Provisional application No. 61/567,981, filed on Dec. 7, 2011.

(51) Int. Cl.
| | | |
|---|---|---|
| *C07F 9/10* | (2006.01) | |
| *C12P 7/64* | (2006.01) | |
| *C11C 3/10* | (2006.01) | |
| *A23D 9/013* | (2006.01) | |

(52) U.S. Cl.
CPC ............... *C07F 9/10* (2013.01); *A23D 9/013* (2013.01); *C07F 9/106* (2013.01); *C11C 3/10* (2013.01); *C12P 7/6409* (2013.01); *C12P 7/6481* (2013.01)

(58) Field of Classification Search
CPC .................................. C07F 9/10; C12P 7/6409
USPC .............................. 514/121; 554/79; 435/134
See application file for complete search history.

(56) References Cited

FOREIGN PATENT DOCUMENTS

| | | |
|---|---|---|
| EP | 0 178 624 A2 | 4/1986 |
| WO | 98/40499 A1 | 9/1998 |
| WO | 2007/053800 A2 | 5/2007 |
| WO | 2007/111720 A2 | 10/2007 |

OTHER PUBLICATIONS

Robert B. Layzer, Section Five—Degenerative Diseases of the Nervous System, Cecil Textbook of Medicine, 20th edition (1996), vol. 2, pp. 2050-2057.*
Antonio R. Damasio, Alzheimer's Disease and Related Dementias, Cecil Textbook of Medicine, 20th edition (1996), vol. 2, pp. 1992-1996.*
"FDA mulls drug to slow late-stage Alzheimer's," [retrieved on Sep. 23, 2003]. Retrieved online via Internet, URL: http://www.cnn.com/2003/HEALTH/conditions/09/24/alzheimers.drug.ap/index.html.*
"Autism," [retrieved on May 14, 2008]. Retrieved online via Internet, URL: http://www.nlm.nih.gov/medlineplus/autism.html.*
Banerjee, Rajkumar, et al., "Anisamide-Targeted Stealth Liposomes: A Potent Carrier for Targeting Doxorubicin to Human Prostate Cancer Cells," International Journal of Cancer, vol. 112, No. 4, pp. 693-700 (Nov. 20, 2004).
Johannsson, A., et al., "The Effect of Bilayer Thickness on the Activity of (Na+ and K+)-ATPase," Biochimica et Biophysica Acta, vol. 641, pp. 416-421 (1981).
International Search Report of PCT/US12/068317 dated Jul. 7, 2013.
Written Opinion of PCT/US12/068317 dated Jul. 7, 2013.

* cited by examiner

*Primary Examiner* — Kristin Vajda
(74) *Attorney, Agent, or Firm* — Morgan, Lewis & Bockius LLP; Jeffry S. Mann

(57) ABSTRACT

The present invention concerns phospholipid compositions having a relatively high concentration of compounds of the following structure (I): wherein at least one of $R^1$ and $R^2$ is palmitoleoyl, myristoleoyl or lauroleoyl and methods for their preparation. The present invention also concerns the use of these phospholipid compositions to treat a variety of disorders by administering the composition to a patient in need thereof.

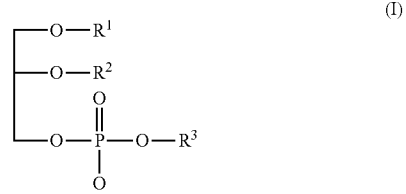

19 Claims, 2 Drawing Sheets

Figure 1. Production of ethyl ester-EPA/DHA concentrates (50% EPA/DHA) and ethyl esters-Omega 7 (30% palmitoleic acid)

PHOSPHOLIPID COMPOSITIONS ENRICHED FOR PALMITOLEIC, MYRISTOLEIC OR LAUROLEIC ACID, THEIR PREPARATION AND THEIR USE IN TREATING METABOLIC AND CARDIOVASCULAR DISEASE

CROSS REFERENCE TO RELATED APPLICATIONS

This application claims the benefit of U.S. Provisional Patent Application No. 61/567,981, filed Dec. 7, 2011, the entire contents of which are incorporated herein by reference.

FIELD OF THE INVENTION

The present invention concerns phospholipid compositions having a relatively high concentration of palmitoleic acid, myristoleic acid or lauroleic acid and methods for their preparation. The present invention also concerns the use of these phospholipid compositions to treat a variety of disorders by administering the composition to a patient in need thereof.

BACKGROUND

Palmitoleic acid (also known as 9-hexadecenoic acid and C16:1 n-7) is an omega-7 monounsaturated fatty acid having the formula $CH_3(CH_2)_5CH=CH(CH_2)_7COOH$. Palmitoleic acid can occur in a cis or trans configuration. In its cis configuration, palmitoleic acid is a common constituent of the glycerides of human adipose (fat) tissue and is found in the lipid bilayer of the cell membrane in all human tissues where it can participate in several metabolic processes.

Myristoleic acid (also known as 9-tetradecenoic acid and C14:1 n-5) is an omega-5 fatty acid produced in nature by the action of delta-9 desaturase on myristic acid. This fatty acid (cis-form) is relatively uncommon in nature. Low concentrations (between 1% and 2%) of myristoleic acid are found in fish oils and dairy butter; however, myristoleic acid is present in quite high concentration in the seed oil from plants of the genus Myristicaceae. Myristoleic acid has anti-inflammatory and analgesic properties and appears to slow prostate tumor growth. Omega-5 fatty acids are understood to be effective in treating and/or preventing a variety of diseases including cardiovascular and skin disorders as well as certain types of cancer as well as certain psychiatric and cognitive disorders.

Lauroleic acid (also known as 9-dodecenoic acid and C12:1 n-3) is an omega-3 fatty acid. This fatty acid (cis-form) is also relatively uncommon in nature, found in small amounts in animal fats and milk lipids. Lauroleic acid is a natural metabolite of lauric acid in rat hepatocytes (Legrand P et al., Lipids, 37:569 (2002)). Omega-3 fatty acids are understood to be effective in treating cardiovascular, inflammation and cancer Recent studies indicate that cis-palmitoleic acid may have protective effects against some cardiovascular disease risk factors. For example, higher concentration of circulating cis-palmitoleic acid is associated with lower LDL cholesterol (often referred to as "bad" cholesterol), higher HDL cholesterol (often referred to as "good" cholesterol), and lower total HDL-cholesterol ratio. (Mozaffarian et al., Am. J. Clin. Nutr., 92(6):1350-1358 (2010)). Published data show that diets enriched for macadamia nuts, a rich natural source of cis-palmitoleic acid, result in significantly lower plasma total cholesterol and LDL cholesterol in men and women and in controlled lab animal studies (Curb et al., Arch. Intern. Med., 160:1154-1158 (2000); Matthan et al, J. Nutr., 139(2):215-221 (2009); Griel et al., J. Nutr., 138:761-767 (2008)). The hypocholesterolemic effect of dietary monounsaturated fatty acids such as cis-palmitoleic acid has been attributed to up-regulation of LDL receptor activity. Monounsaturated fatty acids are preferred substrates for acyl CoA:cholesterol acyltransferase, which catalyzes the esterification of hepatic free cholesterol to an inert cholesterol ester pool. This in turn reduced the putative regulatory pool of intracellular free cholesterol, increasing LDL receptor activity and subsequently decreasing circulating cholesterol concentrations (Griel et al., 2008; Mozaffarian, 2010).

Studies also indicate that cis-palmitoleic aid promotes beta-cell proliferation, and facilitates production of glucagon-like peptide-1 (GLP-1), an incretin hormone that enhances the glucose-dependent secretion of insulin from Beta-cells. (Maedler et al., Diabetes, 50:69-76 (2001)); Free fatty acids regulate gut incretin glucagon-like peptide-1 secretion through GPR120 (Hirasawa et al., Nature Medicine, 11(1):90-94 (2005)). Increased cis-palmitoleic acid level is also observed in the newborn in response to oxidative stress. (Hara et al., Biochemical and Biophysical Research Communications, 257(1):244-248 (1999)).

Recent studies have found that trans-palmitoleic acid levels are inversely associated with new-onset (type 2) diabetes and other metabolic risk factors and tends to promote healthy levels of blood cholesterol (Mozaffarian et al., Ann. Intern. Med., 153(12):790-799 (2010)). Moreover, the trans-configuration of palmitoleic acid may be more bioactive than the cis-configuration.

Cis-palmitoleic acid can be obtained in the diet, e.g. from fish, plants and nuts enriched for this fatty acid. For example, buckthorn oil and macadamia oil are known to be enriched for cis-palmitoleic acid. Alternatively, extracts containing cis-palmitoleic acid can be obtained from marine or aquatic biomass as described in U.S. Patent Appl. Pub. No. 2004/0234587, the contents of which are incorporated herein by reference. Trans-palmitoleic acid is not endogenously produced in humans but is a component of dairy products such as milk, yogurt and cheese; accordingly, extracts containing trans-palmitoleic acid may be obtained from these sources.

Fatty acids in the form of phospholipids are reported to be more readily absorbed and also to be more bioactive. Palmitoleic acid, myristoleic acid and lauroleic acid obtained from fish or plant extract is not especially suitable for use in the modern food/medicine industries. For example, cis-palmitoleic acid, in the form of phospholipid, is present as only a small percentage of the total lipids found in fish, plants or nuts enriched for this fatty acid. Moreover, phospholipids extracted from natural sources, especially marine sources, come with characteristic tastes and smell which reduces their appeal in food applications.

Therefore, there is a need for compositions having a relatively high bioavailable concentration of palmitoleic acid, myristoleic acid and lauroleic acid in the form of phospholipid, and a commercially viable method for its production.

SUMMARY OF THE INVENTION

In one embodiment, a phospholipid composition is provided comprising one or more compounds of Formula I:

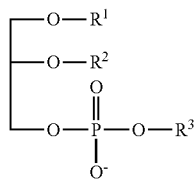

wherein $R^1$ and $R^2$ are each independently selected from —COOH or an acyl radical of any fatty acid, wherein at least one of $R^1$ and $R^2$ is an acyl radical of trans- or cis-palmitoleic acid, trans- or cis-lauroleic myristoleic acid or trans- or cis-lauroleic acid and $R^3$ is selected from H, ethanolamine, choline, serine, or inositol, characterized in that palmitoleic acid constitutes at least 5%, preferably at least 10%, more preferably at least 20% and even at least 50% weight percentage based on the total fatty acid content of the total phospholipid fraction of the composition. In a preferred embodiment, at least one of $R^1$ and $R^2$ and more preferably both is an acyl radical of trans- or cis-palmitoleic acid.

In another embodiment, a method of producing a phospholipid composition containing a relatively high concentration of phospholipids having palmitoleic acid, myristoleic acid or lauroleic acid incorporated at the sn-1 and/or sn-2 position is provided comprising (i) esterification of oil derived from a palmitoleic acid-, myristoleic acid- or lauroleic acid-rich source with ethanol to form ethyl esters and (ii) lipase and/or phospholipase A2 (PLA2) catalyzed acidolysis between the ethyl esters and a phospholipid. In a preferred embodiment, oil derived from a palmitoleic acid-rich source such as menhaden is esterified with ethanol to form ethyl esters.

In another embodiment, the composition is formulated as a pharmaceutical or nutraceutical composition optionally comprising one or more pharmaceutically acceptable carriers.

In another embodiment, a method for preventing and/or treating a cardiovascular disease is provided comprising administering an effective amount of the composition to a subject in need of such treatment.

In another embodiment, a method for preventing and/or treating metabolic syndrome or an associated condition is provided comprising administering an effective amount of the composition to a subject in need of such treatment.

In another embodiment, a method for preventing and/or treating a skin condition is provided comprising administering an effective amount of the composition to a subject in need of such treatment.

In another embodiment, a method for preventing and/or treating an inflammatory disorder including without limitation rheumatoid arthritis and osteoarthritis is provided comprising administering an effective amount of the composition to a subject in need of such treatment.

In yet another embodiment, a method for preventing and/or treating a cognitive disorder is provided comprising administering an effective amount of the composition to a subject in need of such treatment.

DETAILED DESCRIPTION OF THE PREFERRED EMBODIMENTS

Figure 1:
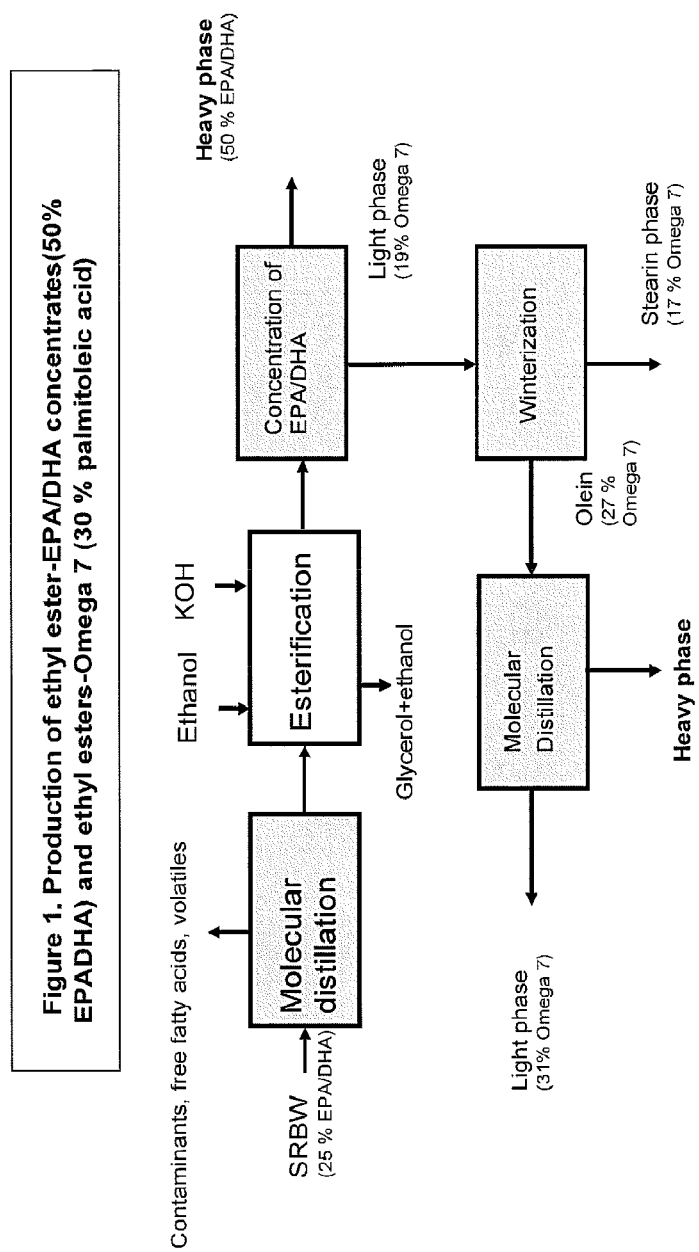
FIG. 1 is a flowchart illustrating steps in a preferred method for producing concentrated palmitoleic acid ethyl esters. Briefly, oil extract obtained by conventional methods from menhaden fish is subjected to (i) molecular distillation to remove contaminants and free fatty acids (ii) esterification using ethanol and an alkaline catalyst to form ethyl esters (iii) molecular distillation to separate lighter ethyl esters (enriched for palmitoleic acid) from heavier ethyl esters (enriched for eicosapentaenoic acid (EPA)/docosahexaenoic acid (DHA)) and (iv) crystallization and molecular distillation to further concentrate the palmitoleic acid ethyl esters to over 30%.

While the present invention is capable of being embodied in various forms, the description below of several embodiments is made with the understanding that the present disclosure is to be considered as an exemplification of the invention, and is not intended to limit the invention to the specific embodiments illustrated.

It is to be understood that any ranges, ratios and ranges of ratios that can be formed by any of the numbers or data present herein represent further embodiments of the present invention. This includes ranges that can be formed that do or do not include a finite upper and/or lower boundary. Accordingly, the skilled person will appreciate that many such ratios, ranges and ranges of ratios can be unambiguously derived from the data and numbers presented herein and all represent embodiments of the present invention.

Before the present compounds, products and compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictate otherwise.

Definitions

The term "fatty acid" as used herein means a carboxylic acid with a long unbranched aliphatic chain which is either saturated or unsaturated (e.g. mono or polyunsaturated). Saturated fatty acids have the general formula $C_nH2_n+1$COOH and include, without limitation, propanoic acid, butanoic acid, pentanoic acid and the like. An unsaturated fatty acid has one or more double bonds in the fatty acid chain. A fat molecule is monounsaturated if it contains one double bond and polyunsaturated if it contains two or more double bonds. Examples of unsaturated fatty acids include, without limitation, myristoleic acid, palmitoleic acid, sapienic acid, oleic acid, linoleic acid, arachidonic acid, eicosapentaenoic acid (EPA), docosahexaenoic acid (DHA) and docosapentaenoic acid.

The term "palmitoleic acid" or "palmitoleoyl" refers to 9-hexadecenoic acid having 16 carbon atoms and one double bond ($CH_3(CH_2)_5CH=CH(CH_2)_7COOH$) and encompasses both the cis (Z) and trans (E) configurations unless otherwise specified.

The term "lauroleic acid" refers to 9-dodecenoic acid having 12 carbon atoms and one double bond and encompasses both the cis (Z) and trans (E) configurations unless otherwise specified.

The term "myristoleic acid" refers to 9-tetradecenoic acid having 14 carbon atoms and one double bond and encompasses both the cis (Z) and trans (E) configurations unless otherwise specified.

A "subject" is a mammal, e.g. a human, mouse, rat, guinea pig, dog, cat, horse, cow, pig or non-human primate, such as a monkey, chimpanzee, baboon or rhesus.

An "effective amount" or "effective dosage" means an amount of a composition described herein sufficient to treat a particular condition.

The term "treat" or "treatment" refers to improving at least one symptom of a subject's disorder. Treatment includes, but is not limited to, curing the disorder or disease, arresting the development of the disorder or disease; at least partially ameliorating the disorder or disease, and relieving at least one condition caused by the disease or disorder.

Compositions

In various embodiments, phospholipid compositions comprising one or more compounds of Formula I:

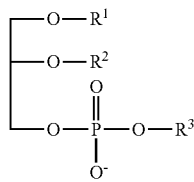

are provided wherein $R^1$ and $R^2$ are each independently selected from —COOH or an acyl radical of any fatty acid, wherein at least one of $R^1$ and $R^2$ is palmitoleoyl, myristoleoyl or lauroleoyl (each in the cis or trans configuration), and $R^3$ represents H, —CH$_2$CH$_2$NH$_3$ (ethanolamine), —CH$_2$CH$_2$N(CH$_3$)$_3$ (choline), CH$_2$CHNH$_3$CO$_2$H (serine), or PO$_3$(CHOH)$_6$ (inositol), characterized in that palmitoleic acid, lauroleic acid or myristoleic acid constitutes at least 5% weight percentage based on the total fatty acid content of the total phospholipid fraction of the composition. Preferably, palmitoleic acid, lauroleic acid or myristoleic acid constitutes at least 7% weight percentage based on the total fatty acid content of the total phospholipid fraction of the composition, and even more preferably constitutes at least 8%, 9%, 10%, 11%, 12% 13%, 14%, 15%, 16%, 17%, 18%, 19%, 20%, 25%, 30%, 40%, 45%, 50%, 60%, 70%, 80% and even at least 90% weight percentage based on the total fatty acid content of the total phospholipid fraction of the composition. In related embodiments, palmitoleic acid, lauroleic acid or myristoleic acid constitutes from about 5% to about 80%, from about 10% to about 70%, from about 15% to about 60%, from about 20% to about 50% or from about 30% to about 40% weight percentage based on the total fatty acid content of the total phospholipid fraction of the composition. According to a particularly preferred embodiment, palmitoleic acid constitutes from about 30% to about 50% weight percentage based on the total fatty acid content of the total phospholipid fraction of the composition.

In other embodiments, the compositions are characterized in that the one or more compounds of Formula I are present in at least 5% weight percentage of the total phospholipid fraction of the composition, preferably in at least 10% weight percentage, more preferably in at least 20% weight percentage, even more preferably in at least 30% weight percentage or even at least 50% weight percentage of the total phospholipid fraction of the composition.

In some embodiments, $R^1$ is palmitoleoyl, myristoleoyl or lauroleoyl, $R^2$ is —COOH or an acyl radical of a fatty acid other than palmitoleic acid, myristoleic acid or lauroleic acid and $R^3$ is as described above.

In a preferred embodiment, $R^1$ is cis-palmitoleoyl, $R^2$ is —COOH or an acyl radical of a fatty acid other than palmitoleic acid and $R^3$ is as described above:

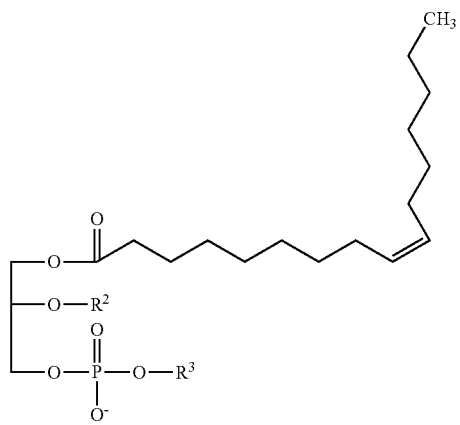

In one embodiment, $R^1$ is palmitoleoyl, myristoleoyl or lauroleoyl and $R^2$ is an acyl radical of a monounsaturated fatty acid such as C18:1. In another embodiment, $R^1$ is palmitoleoyl, myristoleoyl or lauroleoyl and $R^2$ is an acyl radical of a saturated fatty acid such as C16:0 or C18:0. In another embodiment, $R^1$ is palmitoleoyl myristoleoyl or lauroleoyl and $R^2$ is an acyl radical of a polyunsaturated fatty acid such as C18:2 or C18:3.

In other embodiments, $R^2$ is palmitoleoyl, myristoleoyl or lauroleoyl, $R^1$ is —COOH or an acyl radical of a fatty acid other than palmitoleic acid, myristoleic acid or lauroleic acid and $R^3$ is as described above.

In a preferred embodiment, $R^2$ is cis-palmitoleoyl, $R^1$ is —COOH or an acyl radical of a fatty acid other than palmitoleic acid and $R^3$ is as described above:

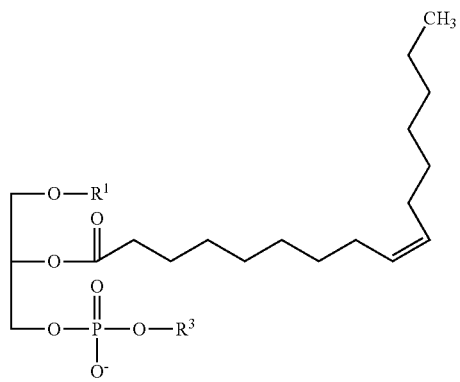

In one embodiment, $R^2$ is palmitoleoyl, myristoleoyl or lauroleoyl and $R^1$ is an acyl radical of a monounsaturated fatty acid such as C18:1. In another embodiment, $R^2$ is palmitoleoyl, myristoleoyl or lauroleoyl and $R^1$ is an acyl radical of a saturated fatty acid such as C16:0 or C18:0. In another embodiment, $R^2$ is palmitoleoyl, myristoleoyl or lauroleoyl and $R^1$ is an acyl radical of a polyunsaturated fatty acid such as C18:2 or C18:3.

In a particularly preferred embodiment $R^1$ and $R^2$ are each palmitoleoyl, myristoleoyl or lauroleoyl and $R^3$ is selected from H, ethanolamine, choline, serine, or inositol. In another particularly preferred embodiment, $R^1$ and $R^2$ are each cis-palmitoleoyl and $R^3$ is choline:

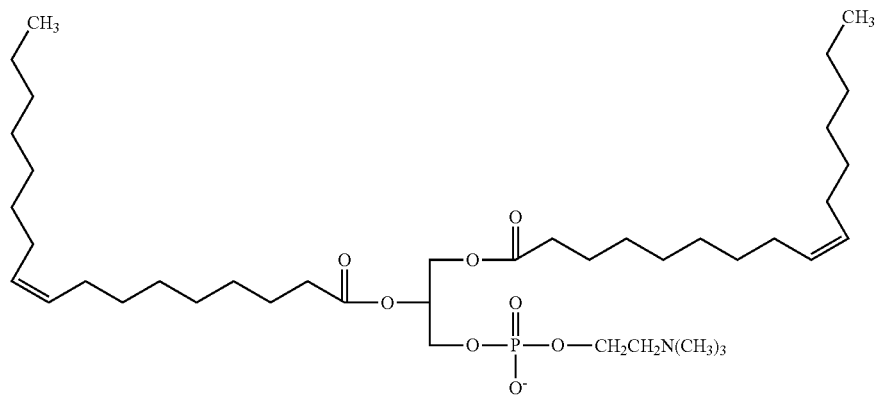

Acyl radicals for $R^1$ and $R^2$ are those of any fatty acid, whether saturated, monounsaturated or polyunsaturated. For example, $R^1$ and $R^2$ may be, independently, butyryl, pentanoyl, caproyl, heptanoyl, hexanoyl, octanoyl, nonanoyl, lauroyl, myristoyl, palmitoyl, stearoyl, oleoyl, linoleoyl, arachidonoyl, eicosapentaenoyl, docosahexaenoyl and docosapentaenoyl. In one preferred embodiment, $R^1$ and $R^2$ are each independently a saturated or unsaturated acyl residue containing 8 to 24 carbons.

In some embodiments, the bioavailability of palmitoleic acid, myristoleic acid or lauroleic acid is increased in phospholipid compositions of the invention as compared to purified triglycerides having substantially the same weight percentage of palmitoleic acid.

Preparation

Compositions of the invention may be produced by any method known in the art, but preferably are produced by the esterification of oil derived from a myristoleic acid-, lauroleic acid- or palmitoleic acid-rich source with ethanol to form ethyl esters followed by lipase and/or PLA2 catalyzed acidolysis between the ethyl esters and a phospholipid.

Any natural source of palmitoleic acid, myristoleic acid or lauroleic acid may be exploited to obtain oil for use according to the method. Preferred natural sources of palmitoleic acid include, without limitation, menhaden fish, macademia nuts and sea buckthorn, as these sources contain relatively high concentrations of palmitoleic acid. Preferred natural sources of myristoleic acid include beef tallow and seeds of *Pycnanthus Kombo*. Preferred natural sources of lauroleic acid include milk lipids.

Oil obtained from a palmitoleic acid-, myristoleic acid- or lauroleic acid-rich source contains fatty acids primarily in the form of triglycerides (three fatty acids esterified to a glycerol backbone). Free fatty acids and other contaminants in the oil such as dioxins and heavy metals may be removed by molecular distillation. The distilled oil is then reacted with ethanol in the presence of a catalyst, preferably a strong alkaline such as potassium hydroxide, to produce ethyl esters. During this process (esterification), the alcohol is deprotonated with a base to make it a stronger nucleophile. Preferably, the reaction occurs under heated conditions to accelerate the reaction.

The resulting ethyl esters are then subjected to molecular distillation and the palmitoleic acid, myristoleic acid or lauroleic acid containing fraction is collected. For example, when menhaden is used as a source of palmitoleic acid, distillation of the oil results in two streams: a heavy phase rich in omega 3 ethyl esters (constituting about 50% EPA/DHA) and a light phase rich in shorter chain fatty acid ethyl esters of myristic, palmitoleic, palmic and oleic acids (constituting about 20% palmitoleic acid).

Optionally, the palmitoleic acid, myristoleic acid or lauroleic acid ethyl esters may be further concentrated through one or more purification steps. In a preferred embodiment, the acid ethyl ester-enriched light phase obtained in the previous step is subjected to crystallization (or winterization) in order to remove the more saturated fatty acids such as myristic and palmitic acid. In another preferred embodiment, palmitoleic acid ethyl esters are further concentrated by molecular distillation. In a particularly preferred embodiment, palmitoleic acid is concentrated to about 30% by employing crystallization and molecular distillation sequentially on the palmitoleic acid ethyl ester-enriched light phase. Further purification by, e.g. urea crystallization and/or preparatory chromatography may concentrate palmitoleic acid to over 50%.

Palmitoleic acid, myristoleic acid or lauroleic in the concentrated ethyl esters is then incorporated into phospholipids at the sn-1 and/or sn-2 positions by acidolysis reaction catalyzed by a 1,3-regiospecific lipase having phospholipase activity and/or phospholipase A2 (PLA2) to produce compositions of the invention.

Lipases are enzymes that normally catalyze the hydrolysis of ester chemical bonds in lipid substrates in a water-rich medium. In a water-starved medium, these lipases catalyze the esterification or interesterification of fatty acids into triglycerides or phospholipids. Any 1,3-regiospecific lipase having phospholipase activity may be employed in the method including, without limitation, *Rhizomucor miehei* lipase (Lipozyme® RM IM), *Thermomyces lanuginose* (Lipozyme® TL IM), *Rhizopus orizae* (lipase F-Ap15), *Rhizopus delemar* lipase, *Mucor javanicus* lipase and *Candida cylindracea* lipase, in order to replace fatty acids at the $R^1$ (=sn-1) position of a phospholipid with palmitoleic acid, myristoleic acid or lauroleic acid.

Phospholipase A2 (PLA2) catalyzes the hydrolysis of ester chemical bonds at the $R^2$ (=sn-2) position of a phospholipid. PLA2 for use in the invention may be obtained from any natural or commercial source, e.g. Lecitase 10 L from porcine pancreas (Novozymes®).

A 1,3-regiospecific lipase or PLA2 may be employed separately, in order to catalyze the incorporation of palmitoleic acid, myristoleic acid or lauroleic acid only at the $R^1$ or $R^2$ position, respectively, of the phospholipid, but are preferably employed together in order to catalyze the incorporation of palmitoleic acid, myristoleic acid or lauroleic acid at both the $R^1$ and $R^2$ positions in which case the 1,3-regiospecific lipase and PLA2 may be employed sequentially (i.e. in separate reactions) or may be employed together in the same reaction.

A variety of phospholipids may be interesterified according to the methods to produce phospholipid compositions of the invention, including without limitation glycerophospholipids such as phosphatidic acid, phosphatidylcholine, phosphatidylethanolamine, phosphatidylserine, and phosphatidylinositol and phosphosphingolipids such as a sphingomyelin. The phospholipids may be used individually or in combinations and may be obtained from natural sources. In a preferred embodiment, the phospholipid composition is obtained by interesterifying lecithin, such as soybean lecithin, with palmitoleic-acid enriched ethyl esters from menhaden oil.

Therapeutic Methods

In one embodiment, a method for preventing and/or treating a cardiovascular disease is provided comprising administering an effective amount of a composition of the invention to a subject in need thereof. In related embodiments, a method for preventing and/or treating a disorder selected from the group consisting of low HDL levels, high LDL levels, hypertriglyceridemia, hypercholesterolemia and atherosclerosis is provided comprising administering an effective amount of a composition of the invention to a subject in need thereof.

In another related embodiment, a method for increasing the HDL/LDL ratio in a subject in need thereof is provided comprising administering an effective amount of a composition of the invention to a subject in need thereof.

In another related embodiment, a method for reducing circulating plasma concentrations of triglycerides and/or LDL-cholesterol is provided comprising administering to a subject in need thereof an effective amount of a composition of the invention.

In other embodiments, a method for preventing and/or treating a metabolic syndrome is provided comprising administering an effective amount of a composition of the invention to a subject in need thereof.

In a related embodiment, a method for preventing and/or treating obesity is provided comprising administering an effective amount of a composition of the invention to a subject in need thereof.

The capacity to produce insulin is determined by total β-cell number which is in turn influenced by β cell production and apoptosis. Failure to produce β cells and/or increased apoptosis of β cells can lead to type 2 diabetes. Palmitoleic acid has been shown to stimulate production of β cells without affecting apoptosis. Accordingly, in another related embodiment, a method for preventing and/or treating type 2 diabetes is provided comprising administering to a subject in need thereof a composition of the invention comprising an effective amount of palmitoleic acid.

In yet another related embodiment, a method for treating metabolic syndrome is provided comprising administering an effective amount of a composition of the invention to a subject in need thereof.

In another related embodiment, a method for preventing the transition from metabolic syndrome to type 2 diabetes is provided comprising administering an effective amount of a composition of the invention to a subject in need thereof.

In another related embodiment, a method for treating insulin resistance is provided comprising administering an effective amount of a composition of the invention to a subject in need thereof.

In another related embodiment, a method for stimulating β-cells in vitro is provided comprising contacting pancreatic cells in vitro with an amount of a composition of the invention effective to stimulate the proliferation of said β-cells. The β-cells may be a primary culture of human pancreatic cells obtained from a subject with type 1 diabetes mellitus in which case the thus-treated pancreatic cells may optionally be transplanted (e.g. parenterally) in said subject in order to treat the type 1 diabetes mellitus.

In other embodiments, a method for treating a skin disorder selected from the group consisting of eczema, psoriasis, rosacea, and dry skin is provided comprising administering an effective amount of a composition of the invention to a subject in need thereof.

In other embodiments, compositions of the invention may be administered in order to reduce oxidative stress. In a related embodiment, compositions of the invention may be administered to ameliorate the effects of aging.

In other embodiments, compositions of the invention may be administered in order to treat an inflammatory disorder including without limitation rheumatoid arthritis and osteoarthritis.

In other embodiments, compositions of the invention may be administered in order to treat a cognitive disorder such Alzheimer's disease.

In other embodiments, a method for treating cancer is provided comprising administering an effective amount of a composition of the invention to a subject in need thereof. In a preferred embodiment, the composition is administered in an amount effective to treat prostate cancer.

In various embodiments, the compositions described herein may be combined with any other recognized treatment regimen in order to treat a disease. The compositions described herein and one or more additional active agents may be administered simultaneously, separately or sequentially in order to treat a disease. For example, a composition of the invention may be combined with insulin in order to treat type 2 diabetes.

Formulations and Dosages

In another embodiment, a pharmaceutical composition is provided comprising one or more compounds of Formula I:

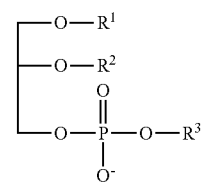

wherein $R^1$ and $R^2$ are each independently selected from —COOH or an acyl of any fatty acid, wherein at least one of $R^1$ and $R^2$ is palmitoleoyl, myristoleoyl or lauroleoyl and $R^3$ is selected from H or choline, ethanolamine, inositol or serine, characterized in that palmitoleic acid, myristoleic acid or lauroleic acid constitutes at least 5% weight percentage, preferably from about 20% or 30% to about 50% weight percentage, based on the total fatty acid content of the total phospholipid fraction of the composition and a pharmaceutically acceptable carrier.

The compositions described herein can be administered via any mode of administration including systemic or local administration such as oral, parenteral, transdermal, subcutaneous or topical.

Depending on the mode of administration, the compositions can be in solid, semi-solid or liquid dosage form. In a preferred embodiment, the pharmaceutical composition is in a form suitable for oral administration such as a tablet or gelatin capsule (comprising the phospholipid composition and optionally a pharmaceutically acceptable carrier). In another embodiment, the composition is in a form suitable for topical administration such as an emulsion (e.g. a cream, ointment, lotion or gel). In another embodiment, the composition is in a form suitable for injection.

Dosage regimens utilizing the compositions described herein can be readily determined by the attending physician taking into account the route of administration, the disorder to be treated, the age, weight, sex and medical condition of the subject. The compositions described herein can be administered as a single daily dose or the total daily dosage may be divided into multiple doses per day. When administered transdermally, the compositions may be administered continuously. When administered otherwise, such as orally, the compositions can be administered daily for a consecutive number of days or can be administered intermittently, for example every other day, weekly (i.e. once per week), bi-weekly, or the like.

An advantage of the method is that it provides palmitoleic acid, as the substrate for the synthesis of phospholipids, from by-products of Omega-3 fatty acid purification, which would otherwise be wasted.

Another advantage of the method is that it provides relatively pure phospholipid palmitoleic acid, myristoleic acid or lauroleic acid products in large quality.

Yet another advantage of the method is that it does not require extreme thermal and pressure reacting conditions during production.

Yet another advantage of method is that it enables production of phospholipids having palmitoleic acid, myristoleic acid or lauroleic acid selectively incorporated at the sn-1 and/or sn-2 position.

Yet another advantage of the method is that it produces phospholipids with higher palmitoleic acid, myristoleic acid or lauroleic acid percentage when comparing with prior disclosed natural or synthesized forms.

Yet another advantage is that the phospholipid palmitoleic acid, myristoleic acid or lauroleic acid compositions of the present invention provide a means for administering these fatty acids with improved bioavailability. Thus, the present compositions provide palmitoleic acid, myristoleic acid or lauroleic acid in a form more effectively digested and absorbed.

Yet another advantage of the method is that it eliminates the odors, tastes and smells, which are commonly associated with phospholipids extracted from natural sources. Further, it eliminates characteristic tastes and smells of phospholipids extracted from marine biomass, making the present compositions particularly suitable for ingestion.

All of the references discussed herein are incorporated by reference in their entirety.

The following Examples are meant to be illustrative of the invention and are not intended to limit the scope of the invention as set out in the appended claims.

Example 1

Process for Preparing Compositions Enriched for Phospholipids Having Cis-Palmitoleic Acid at the Sn1 and/or Sn2 Positions An oil extract was obtained from menhaden fish and determined to contain about 10% palmitoleic acid (in the cis-configuration). Fatty acids in the menhaden oil were then esterified with ethanol in the presence of potassium hydroxide (as a catalyst) to form fatty acid ethyl esters. The resulting fatty acid ethyl esters were then subjected to molecular distillation resulting in two phases: one rich in omega 3 ethyl esters (about 50% eicosapentaenoic acid (EPA)/docosahexaenoic acid (DHA)) and the other rich in shorter chain fatty acid ethyl esters of mysristic, palmitoleic, palmitic and oleic acids. The latter phase, which was determined to contain over 20% palmitoleic acid, was then subjected to crystallization (or winterization) in order to remove the more saturated fatty acids (e.g. myristic and palmitic acids), followed by molecular distillation to further concentrate the palmitoleic acid, as shown in FIG. 1.

Next, the resulting palmitoleic acid-rich fraction of ethyl esters was incorporated into phospholipids (from commercial lecithin (primarily phosphatidylcholine)) to produce novel phospholipid-conjugates. Enzymes, time and temperature parameters were varied in order to increase the yield of the resulting phospholipid-conjugates. In a typical reaction, soy lecithin was mixed with palmitoleic acid-enriched ethyl esters in hexane solvent and 10-20% immobilized lipase and/or PLA2 was added to the reaction mixture. The reaction was carried out at 50° C. to 65° C. for one to two hours. 1,3-regiospecific lipases Novozyme TL IM and Lipase F-AP15 were employed. After the reaction was completed, the enzyme was filtered off and the lecithin-oil mixture was solvent and water washed to separate the phospholipid fraction.

The phospholipid fraction was dried in a vacuum oven overnight and analyzed for palmitoleic acid incorporation by preparative TLC followed by gas chromatographic (GC) analysis. Briefly, reaction products were first separated on preparative TLC plates by developing with the mobile phase chloroform/methanol/water (62:25:4 vol/vol/vol). Part of the plate was carefully cut and eluted compounds were detected by spraying 5% phosphomolybdic acid in ethanol followed by heating. This part of the plate was used as a template to identify the phospholipid classes which were then scraped off from the TLC plates and put into a test tube for fatty acid methyl ester preparation of the individual classes. Fatty acid methyl esters were prepared by adding 1.0 mL 0.25 M sodium methoxide in methanol/diethyl ether (1:1) to the scrapings in test tubes from the TLC plates. After incubation for 5 minutes in a water bath shaker at 45° C., 500 µL hexane was added, followed by 3 mL saturated NaCl solution. After vortexing and centrifugation, another 500 µL of hexane was added and methyl esters extracted in hexane were collected in the upper layer for GC analysis. Phospholipids having up to 50% palmitoleic acid (weight percentage) based on the total fatty acid content of the total phospholipid fraction of the composition were obtained.

Figure 2:
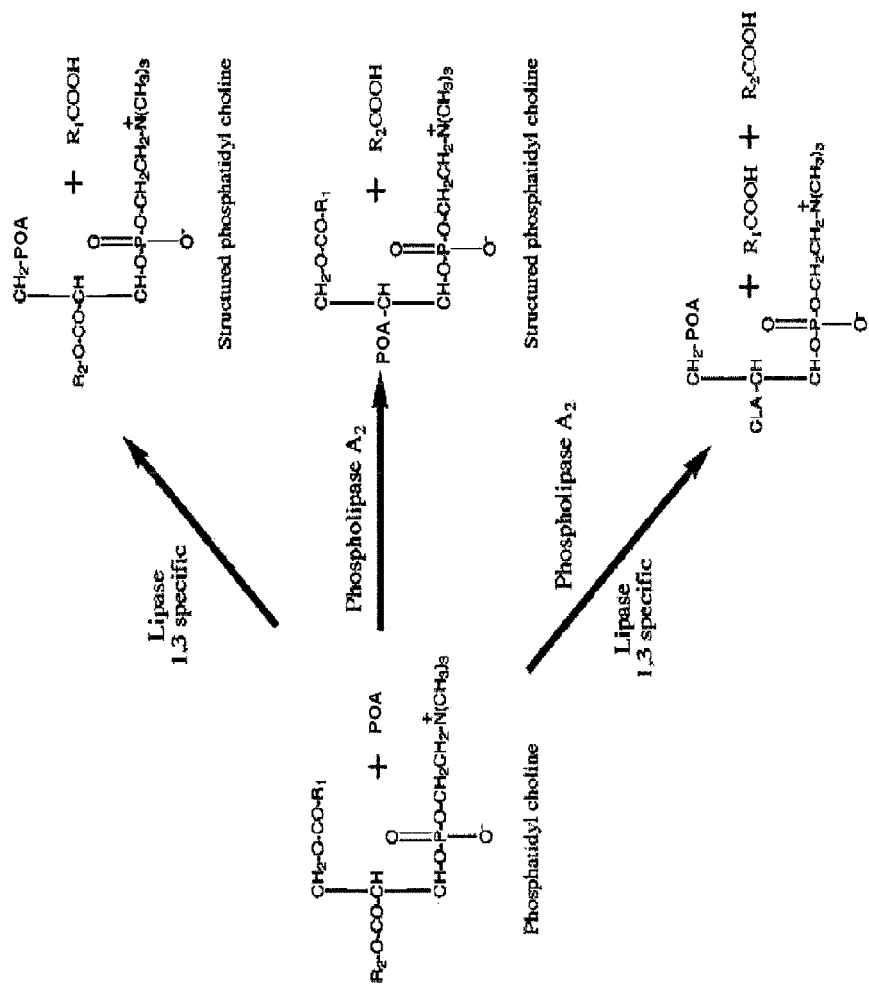
FIG. 2 is a flowchart illustrating the incorporation of palmitoleic acid (POA) of phospholipids (phosphatidylcholine)

Although Novozyme TL IM and Lipase F-AP15 are exemplified, several alternative 1,3-regiospecific lipases may be used as well, as shown in FIG. 2.

Example 2

Process for Preparing Compositions Enriched for Phospholipids Having Cis-Palmitoleic Acid at the Sn1 and/or Sn2 Positions Cis-palmitoleic acid, for example obtained from Menhaden fish as described in Example 1, is subjected to conditions favoring isomerization to the trans-configuration. Such methods are well known in the art and are described in Phillippaerts et al., ChemSusChem 4:684-702 (2011). For example, a selective nickel or nickel-sulfur catalyst may be employed at high temperature and low hydrogen pressure (conditions favoring isomerization rather than hydrogenation). Alternatively, trans-palmitoleic acid may be generated by subjecting cis-palmitoleic acid to low temperature conditions in the presence of iodine and sulfur catalysts. The resulting trans-palmitoleic acid is then incorporated into phospholipids e.g. by the method described in Example 1.

Example 3

Process for Preparing Compositions Enriched for Phospholipids Having Myristoleic Acid at the Sn1 and/or Sn2 Positions An oil extract is obtained from seeds of a member of the Myristicaceae genus (e.g. *Pycnanthus Kombo*). The seeds from members of this genus can contain up to about 30% myristoleic acid. Fatty acids in the seed oil are then esterified with ethanol in the presence of potassium hydroxide (as a catalyst) to form fatty acid ethyl esters. The resulting fatty acid ethyl esters are then subjected to molecular distillation and the myristoleic acid fraction is collected and optionally subjected to crystallization (or winterization) in order to remove saturated fatty acids (e.g. myristic and palmitic acids), followed by molecular distillation to further concentrate the myristoleic acid. The resulting fatty acid esters are then incorporated into phospholipids by the methods described in Example 1.

Example 4

Bioavailability of the Phospholipid Composition

The difference in bioavailability between a composition of the invention and a fish oil is determined using a rat model. Male rats (e.g. Sprague Dawley rats) are given rat feed comprising a predetermined amount of the phospholipid composition obtained according to Example 1, menhaden fish oil extract (comprising about 10% palmitoleic acid in triglyceride form), or neither (control mice). About 30 days after the start of feeding, rats are starved for 12 hours, then anaesthetized (e.g. with carbon dioxide), weighed and euthanized. Blood is collected and centrifuged to separate plasma and blood cells. The amount of palmitoleic acid in plasma from rats in each group is assayed. A higher plasma level of palmitoleic acid indicates higher bioavailability of palmitoleic acid. Palmitoleic acid levels may also be determined in red blood cyles and monocytes.

Total fatty acid profiles for lipids in the brains, adipose tissues, liver, testicles, heart, brain are determined. A higher concentration of palmitoleic acid in lipids from these organs indicates a higher bioavailability of palmitoleic acid.

Example 5

Effect of the Phospholipid Composition on Cardiovascular Parameters

The effect of the phospholipid composition obtained in Example 1 on cholesterol, LDL, HDL, and triglyceride levels is assessed using a rat model (e.g. Sprague Dawley rats). Rats are given rat feed comprising a predetermined amount of the phospholipid composition obtained in Example 1, menhaden fish oil extract (comprising about 10% palmitoleic acid in triglyceride form) or placebo (control mice) for a one month period. Blood serum is collected at the beginning and end of the one month period and a lipid profile is obtained from plasma samples. Glucose levels are also measured.

Example 6

Effect of the Phospholipid Composition on Beta Cell Proliferation

Primary cultures of pancreatic cells are obtained (e.g. from rats) and incubated with the phospholipid composition obtained in Example 1, menhaden fish oil extract (comprising about 10% palmitoleic acid in triglyceride form) or placebo (control mice). Beta-cell proliferation is assessed in each group.

The invention claimed is:

1. A phospholipid composition comprising one or more compounds of Formula

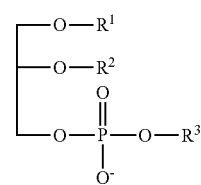

wherein $R^1$ and $R^2$ are each independently selected from —COOH or an acyl radical of any fatty acid, wherein at least one of $R^1$ and $R^2$ is palmitoleoyl, myristoleoyl or lauroleoyl; and $R^3$ is selected from the group consisting of H, —CH$_2$CH$_2$NH$_3$, —CH$_2$CH$_2$N(CH$_3$)$_3$, CH$_2$CHNH$_3$CO$_2$H, and (CHOH)$_6$, characterized in that palmitoleic acid, myristoleic acid or lauroleic acid constitutes at least 15% weight percentage based on the total fatty acid content of the total phospholipid fraction of the composition.

2. The composition of claim 1 wherein at least one of $R^1$ and $R^2$ are palmitoleoyl.

3. The composition of claim 1, wherein $R^1$ and $R^2$ are each palmitoleoyl.

4. The composition of claim 2, wherein at least one palmitoleoyl is in the cis configuration.

5. The composition of claim 2, wherein at least one palmitoleoyl is in the trans configuration.

6. The composition of claim 1, wherein at least one of $R^1$ and $R^2$ are myristoleoyl.

7. The composition of claim 1, wherein at least one of $R^1$ and $R^2$ are lauroleoyl.

8. The composition of claim 1, wherein $R^3$ is —CH$_2$CH$_2$N(CH$_3$)$_3$.

9. The composition of claim 1, wherein palmitoleic acid, myristoleic acid or lauroleic acid constitutes at least 20%, at least 25%, at least 30%, at least 40% or even at least 50% weight percentage based on the total fatty acid content of the total phospholipid fraction of the composition.

10. The composition of claim 9, wherein palmitoleic acid, myristoleic acid or lauroleic acid constitutes between 30% and 60% weight percentage based on the total fatty acid content of the total phospholipid fraction of the composition.

11. The composition of claim 1, wherein the bioavailability of palmitoleic acid, myristoleic acid or lauroleic acid is increased as compared to purified triglycerides having substantially the same weight percentage of palmitoleic acid, myristoleic acid or lauroleic acid.

12. A method for producing a composition of claim 1 comprising:
(a) providing oil obtained from a palmitoleic acid-, myristoleic acid- or lauroleic acid rich source
(b) esterifying said oil with ethanol to form ethyl esters and
(c) incubating said ethyl esters in the presence of a phospholipid, a 1,3-regiospecific lipase having phospholipase activity and/or phospholipase A2 (PLA2) under conditions suitable to catalyze acidolysis between the ethyl esters and the phospholipid to produce a palmitoleic acid-, myristoleic acid- or lauroleic acid-enriched phospholipid composition.

13. The method of claim 12 wherein the 1,3-regiospecific lipase is selected from the group consisting of: *Rhizomucor miehei* lipase, *Thermomyces lanuginose* lipase, *Rhizopus delemar* lipase, *Mucor javanicus* lipase, *Rhizopus orizae* lipase, and *Candida cylindracea* lipase.

14. The method of claim 12 wherein the oil is obtained from a palmitoleic acid-rich source and a palmitoleic acid-enriched phospholipid composition is produced.

15. A pharmaceutical composition comprising a composition according to claim 1 and a pharmaceutically acceptable carrier.

16. A method for treating a disease or disorder comprising administering an effective amount of a composition according to claim 15 to a subject in need thereof, wherein the disease or disorder is selected from the group consisting of: cardiovascular disease, low HDL levels, high LDL levels, hypertriglyceridemia, hypercholesterolemia, atherosclerosis, obesity, prostate cancer, and type 2 diabetes.

17. The method of claim 16, wherein the subject is a human.

18. The method of claim 17, wherein the human is a male.

19. The method of claim 17, wherein the human is a female.

* * * * *